United States Patent [19]
Giuliani et al.

[11] Patent Number: 5,378,153
[45] Date of Patent: Jan. 3, 1995

[54] HIGH PERFORMANCE ACOUSTICAL CLEANING APPARATUS FOR TEETH

[75] Inventors: David Giuliani, Mercer Island; Roy W. Martin, Redmond, both of Wash.

[73] Assignee: GEMTech, Inc., Bellevue, Wash.

[21] Appl. No.: 832,422

[22] Filed: Feb. 7, 1992

[51] Int. Cl.⁶ .............. A61C 15/00; A46B 9/04; A46B 13/00
[52] U.S. Cl. .................. 433/216; 15/167.1; 15/22.1
[58] Field of Search .......... 433/216, 118, 119; 15/22.1, 167.1, 167.2

[56] References Cited

U.S. PATENT DOCUMENTS

| | | | |
|---|---|---|---|
| 1,342,280 | 6/1920 | Fitzgerald . | |
| 1,825,353 | 9/1931 | Johnson . | |
| 2,044,863 | 6/1936 | Sticht | 128/55 |
| 2,196,667 | 4/1940 | Moseley | 15/28 |
| 2,917,758 | 12/1959 | Held et al. | 15/22 |
| 3,227,158 | 1/1966 | Mattingly | 128/66 |
| 3,335,443 | 8/1967 | Parisi et al. | 15/22 |
| 3,488,788 | 1/1970 | Robinson | 15/4 |
| 3,522,801 | 8/1970 | Robinson | 128/66 |
| 3,535,726 | 10/1970 | Sawyer | 15/22 |
| 3,547,110 | 12/1970 | Balamuth | 128/66 |
| 3,636,947 | 1/1972 | Balamuth | 128/66 |
| 3,651,576 | 3/1972 | Massa | 32/40 R |
| 3,676,218 | 7/1972 | Sawyer | 15/22.1 X |
| 3,809,977 | 5/1974 | Balamuth et al. | 318/116 |
| 3,840,932 | 10/1974 | Balamuth et al. | 15/167 R |
| 3,978,852 | 9/1976 | Annoni | 128/62 A |
| 4,071,956 | 2/1979 | Andress | 32/58 |
| 4,144,646 | 3/1979 | Takemoto et al. | 32/40 R |
| 4,192,035 | 3/1980 | Kuris | 15/22 R |
| 4,291,017 | 9/1981 | Beierle et al. | 433/119 X |
| 4,326,314 | 4/1982 | Moret et al. | 15/22 R |
| 4,331,422 | 5/1982 | Heyman | 433/125 |
| 4,333,197 | 6/1982 | Kuris | 15/22 R |
| 4,374,354 | 2/1983 | Petrovic et al. | 320/2 |
| 4,397,055 | 8/1983 | Cuchiara | 15/22 R |
| 4,420,851 | 12/1988 | Wiener | 15/22 R |
| 4,458,374 | 7/1984 | Hukuba | 15/22 R |
| 4,506,400 | 3/1985 | Klein | 15/22 R |
| 4,698,869 | 10/1987 | Mierau et al. | 15/22 R |
| 4,787,847 | 11/1988 | Martin et al. | 433/119 |
| 4,871,396 | 10/1989 | Tsujita et al. | 433/216 X |
| 4,880,382 | 11/1989 | Moret et al. | 433/118 |
| 4,903,687 | 2/1990 | Lih-Sheng | 128/66 |
| 4,903,688 | 2/1990 | Bibby et al. | 128/66 |
| 5,120,460 | 6/1992 | Asai et al. | 433/216 X |
| 5,150,492 | 9/1992 | Suroff | 15/22.1 |
| 5,189,751 | 3/1993 | Guiliani et al. | 15/22.1 |

*Primary Examiner*—Gene Mancene
*Assistant Examiner*—Nicholas D. Lucchesi
*Attorney, Agent, or Firm*—Jensen & Puntigam

[57] ABSTRACT

The dental hygiene apparatus includes a body portion (12) from one end of which extends a elongated resonator arm (32). The arm (32) is mounted for oscillating action about a torsion pin (38), by means of a electromagnet (16) in the body acting in combination with two permqanent magnets (34, 35) which are mounted on the rear end (31) of the resonator arm (32). On the forward end (44) of the resonator arm (32) is mounted a set of bristles (47). The arm (32) is driven such that the tips of the bristles operate within ranges of amplitude and frequency to produce a bristle tip velocity greater than 1.5 meters per second, producing a significant cleansing effect beyond the tips of the bristles.

35 Claims, 3 Drawing Sheets

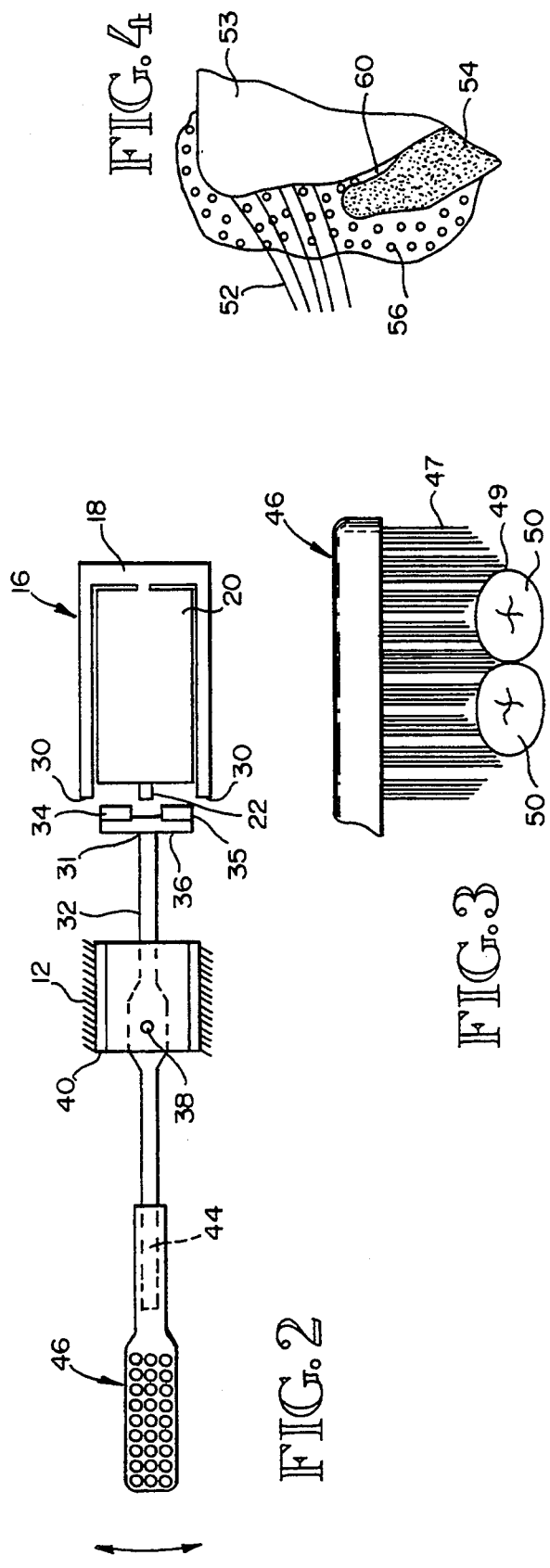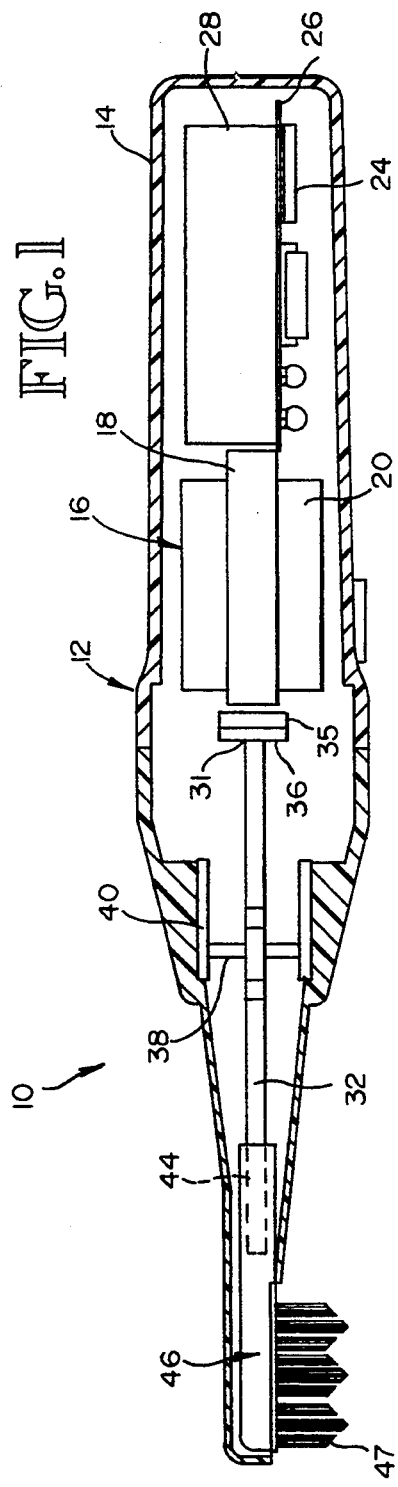

RATE OF BACTERIAL DISLODGMENT

SHEAR STRESS $\tau$ $\tau$ crit

HIGH PERFORMANCE ACOUSTICAL CLEANING APPARATUS FOR TEETH

TECHNICAL FIELD

This invention relates generally to dental hygiene devices and more specifically concerns a power-driven acoustic toothbrush having a selected range of bristle tip velocities so as to produce high performance results.

BACKGROUND OF THE INVENTION

Conventional toothbrushes, including both manual and power-driven embodiments, attempt to produce the desired cleansing effect by scrubbing the surfaces of the teeth to remove dental plaque. Flossing is typically recommended in addition to brushing to reach those tooth areas which cannot be reached by a brush.

However, it is well-known that flossing is inconvenient and difficult to perform. Consequently, only about 15% of the population practice flossing regularly. In addition, conventional brushing action, particularly over an extended period of time, can result in undesirable wear on teeth surfaces.

In order to improve on the brushing/flossing combination, a number of different technical approaches have been used, with varying success. A first category or group of devices involves the water jet phenomenon. Representative examples of patents in this group include U.S. Pat. No. 3,227,158, to Moret, and U.S. Pat. No. 3,522,801 to Robinson. Typically, these devices use a pulsating, highly directed stream of fluid to remove material from around the teeth. However, these devices do have significant disadvantages, including a requirement of relatively high water pressure. Generally, these devices are not very effective in removing plaque. In addition, bacteremia sometimes results from use of these devices. Further, a water jet device is powered by line voltage (not batteries), and typically requires a significant amount of shelf space.

A second group of devices includes those in which a brush is vibrated at an ultrasonic frequency rate to produce a cavitation effect which in turn results in the desired cleansing. U.S. Pat. No. 3,335,443 to Parisi and U.S. Pat. No. 3,809,977 to Balamuth are examples of such devices. The primary difficulty with such devices is the requirement of providing energy through the bristles at ultrasonic frequencies, which are substantially higher than the resonant frequency of the bristles, resulting in very low efficiency of energy transfer to the tips of the applicator. Safety problems may also be significant with such devices, due to the application of ultrasonic energy to tissue.

In still another group are devices which operate at low sonic frequencies but which also allegedly produce a cavitation effect. U.S. Pat. Nos. 3,535,726 and 3,676,218, both to Sawyer, are representative of this group. It is questionable, however, that a vaporous cavitation effect is actually produced by these devices, particularly for those which are hand held and indicated to be powered by batteries.

Lastly, some devices operate in the low audio frequency range (200-500 Hz), and produce what is characterized as mild cavitation, combining that effect with conventional bristle scrubbing action to achieve cleansing. An example of such a device is shown in U.S. Pat. No. 4,787,747 to Martin et al. This device is effective at least to some extent in disrupting plaque colonies. However, the "cavitation" produced by this device, which in fact is not vaporous cavitation (vaporous cavitation being often referred to as "true" cavitation) does not extend beyond the tips of the bristles, and therefore the device is not particularly effective in the inter-dental and subgingival areas of the teeth where enhanced cleansing is needed.

Accordingly, there remains a need for a toothbrush device which has a significant cleaning effect beyond the tips of the bristles, reaching important areas such as the interdental and subgingival regions, yet is safe as well as convenient to use.

DISCLOSURE OF THE INVENTION

Accordingly, the invention is a dental hygiene device for cleaning teeth and interdental and gingival areas, including: a body member which includes an arm mounted for movement, typically some form of oscillating movement; a set of bristles which are located in the vicinity of one end of the arm; and means in the body member for moving the arm and hence the bristles such that the tips of the bristles move at a velocity greater than 1.5 meters per second, sufficient to produce a cleansing action with a dentrifrice fluid beyond the tips of the bristles. Further, the invention includes a method using such a toothbrush in which dental fluid is provided in the vicinity of the teeth and interdental and gingival areas to be cleaned; and the arm and hence the bristles are moved such that the tips of the bristles move through the fluid at a velocity greater than 1.5 meters per second.

BRIEF DESCRIPTION OF THE DRAWINGS

FIG. 1 is a side elevational view of the toothbrush of the present invention, showing the basic elements of the toothbrush.

FIG. 2 is a top plan view of the toothbrush of FIG. 1.

FIG. 3 is a top plan view showing the bristles of the toothbrush of the present invention in position relative to two adjacent teeth.

FIG. 4 is a side elevational view showing the action of the bristles of the toothbrush of the present invention relative to dental fluid and the teeth being cleaned.

BEST MODE FOR CARRYING OUT THE INVENTION

Figure 5:
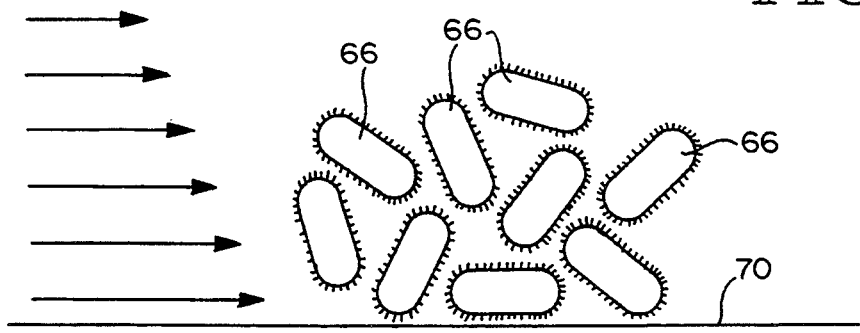
FIG. 5 is a schematic view showing the effect of bristle action of the present invention on teeth bacteria.

FIGS. 1 and 2 show the toothbrush of the present invention, generally at 10. The operational effect of the toothbrush, as described hereinafter, is that, by using selected bristle frequency and amplitude ranges, a significant cleansing effect is produced beyond the tips of the bristles, reaching into interdental and subgingival regions, through a layer of dental fluid, to bacterial plaque on the teeth. This effect is in addition to the conventional scrubbing effect produced by the motion of the bristles when they are in actual physical contact with the teeth to be cleaned.

The toothbrush 10 includes a body 12 which in turn includes a handle portion 14. An electromagnet 16, which comprises a stack of E-shaped laminations 18 with a coil 20 positioned around the middle leg 22 of the stack of laminations, is mounted within handle 14. Coil 20 is driven by a conventional square wave oscillator, shown generally at 24, which is mounted on a printed circuit board 26 and driven by two AA size batteries 28 in the particular embodiment shown. It should be understood, however, that other driving circuitry could be used. The free end tips 30-30 of the stack of laminations 18 are positioned 1-2 mm away from one end 31 of a resonator arm 32. A pair of permanent magnets 34-35 are mounted on a back iron member 36 which is attached to the one end 31 of resonator arm 32. In the embodiment shown, the permanent magnets are made from neodymium iron boron and are mounted in opposite polarities on the flat back iron member 36. Member 36, in operation, closes the magnetic flux path between electromagnet 16 and the two permanent magnets 34 and 35.

Resonator arm 32 is an elongated steel member, mounted by means of a steel torsion pin 38 to body 12 of the toothbrush. Resonator arm 32 is fixedly secured to torsion pin 38, the ends of which are affixed to a circular collar 40 attached to the body 12. The diameter and length of the torsion pin 38 are selected to provide a spring constant which resonates with the mass and compliance distribution of the remainder of the resonator arm. The resonant frequency of the torsion pin is close to the drive frequency of the apparatus, e.g. 250 Hz. In operation, arm 32 twists the torsion pin 38, with the torsion pin tending to maintain the resonator arm in a center position.

At the other end 44 of resonator arm 32 is a brush head 46. The bristles 47 on the brush head 46 in the embodiment shown are made of and are approximately 0.5-0.2 mm in diameter extending substantially perpendicularly relative to the arm 32, and the tips are formed into a scalloped pattern, as shown most clearly in FIG. 1, such that the bristle tips fit into the interdental crevices between teeth. There is typically a distance of 5-8 mm between successive peaks of the scalloped tips and a distance of approximately 1.5-3 mm between the tallest and shortest bristles. In operation, the brush of FIGS. 1 and 2 oscillates in an approximate sinusoidal pattern, linearly back and forth about pin 38, within particular frequency and amplitude ranges. The bristle tip position can be described by the following formula: $X(t) = X_0 \sin(2\pi ft)$, where X is bristle tip position, $X_0$ is the amplitude of oscillation, f is the frequency of oscillation in Hz, and t is time. The bristle velocity U(t) has a peak value of $X_0 2\pi f$. Operating parameters, which are discussed in more detail hereinafter, include combinations of amplitudes of up to ±6 mm and frequencies up to 500 Hz, the product of which exceeds a critical value. At typical values of amplitude (2.5 mm) and frequency (250 Hz), the instantaneous velocity of the bristle tips is 3.9 m/s.

Figure 9:
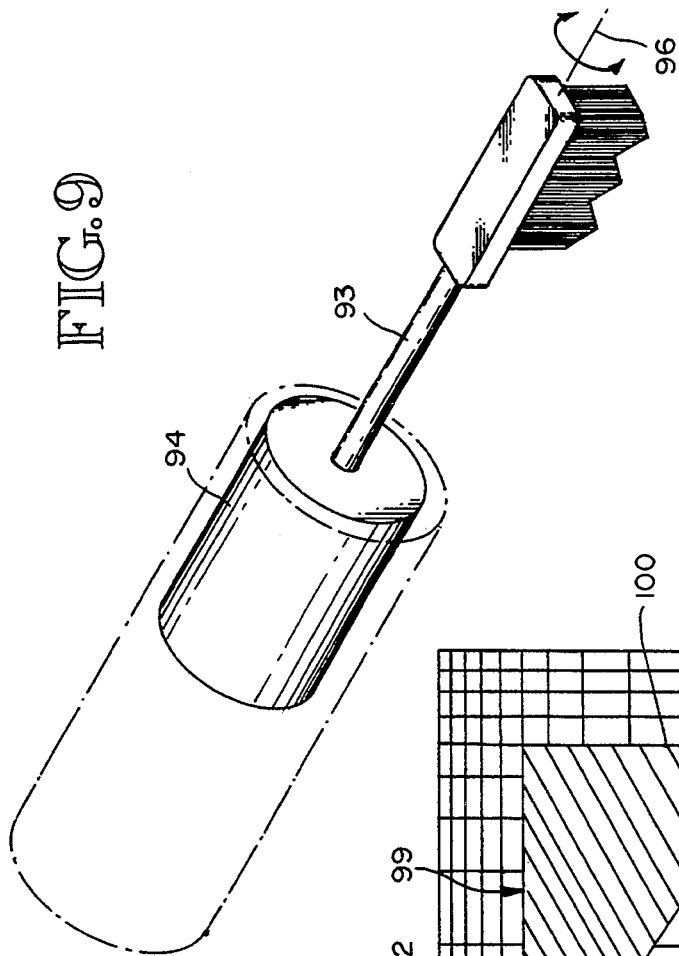
FIG. 9 is an isometric view of a toothbrush of the present invention having a rotational brush action.

FIG. 9 shows a toothbrush similar in effect to that of FIGS. 1 and 2, except that shaft 93 rotates, by action of motor 94, which is mounted in a body 95. Motor 94 rotates shaft 93 about its major axis 96 through an angle $\pm \theta$ (rad.). If the bristle tips are driven at frequencies well below their resonant frequency, the tips move through an arc length of $\pm \theta$ Rb, where Rb is the distance from the free end of the bristles to the axis of rotation 96. When the tips of the bristles are driven at a frequency near the resonant frequency of the bristles, the tips of the bristles move through a larger arc than that provided by the above formula. The movement of the bristles, whether it be linear as for the embodiment of FIGS. 1 and 2, or through an arc, as for FIG. 9, or for some other periodic back and forth reciprocal movement, is generally referred to herein as oscillating movement.

In actual use of the brush 10, as shown representationally in FIG. 3, the toothbrush is held so that the brush head 46 is approximately horizontal, with the tips 49 of the bristles 47 positioned against the side surfaces of the teeth 50, typically near the gum line. As indicated above, the bristles 47 fit around adjacent teeth, into the front portions of the interdental regions between teeth 50. The motion of the brush is up and down, i.e. linearly into and out of FIG. 3, toward and away from the gum line.

FIG. 4 shows the action of bristles 52 of a toothbrush of the present invention in relation to a representative tooth 53, a gum region 54, and a mass of dental fluid 56. As a result of the action of the bristles, pressure in the fluid 56 surrounding the teeth builds up, especially in the area where the gum region 54 meets the teeth. The pressure will reverse, resulting in an alternating pressure field, as the brush sweeps first in one direction and then the opposite direction. The pressure is concentrated on periodontal pocket 60 between the gum region and the tooth, where bacteria are concentrated. The sweeping, back and forth motion of the bristles, towards and away from the gum line, causes the fluid 56 to flow at velocities which are near that of the brush, and maximizes the pressure in the interdental and subgingival regions, beyond the actual reach of the bristles. The dental fluid 56 may be saliva, with additional water or a conventional dentifrice, i.e. toothpaste, or special bacteria-fighting solutions.

This action of the bristles, briefly described above and in more detail below, results in a number of particular acoustical effects beyond the tips of the bristles themselves. It should be understood, however, that while a significant advantage of the toothbrush of the present invention is in its acoustic cleansing effects, the toothbrush is also capable of scrubbing action, which removes plaque mechanically in those areas where the bristles physically contact the dental plaque. The mechanical erosion of plaque is dependent on the actual distance traveled by the tips of the bristles. In the present invention, the toothbrush works best at relatively light loading (pressure against the teeth). Typically this is about 10% of the loading normally encountered in brushing with conventional brushes. This reduction in loading will decrease the abrasion caused by bristle contact but at the same time facilitate the back and forth fluid movement which is important in achieving the desired acoustic effects.

The first significant acoustic effect, involving fluid-coupled effects from the movement of the bristles, concerns acoustical pressure on the plaque. Damage to the plaque results from the alternating pressure field in the dental fluid produced by the bristle movement, which is transmitted to the plaque. The plaque is believed to absorb the vibrational energy produced by the bristles, with resulting damage thereto. Further, the vibrational stress in the plaque allows entry of chemically active agents which may be present in the dental fluid into the interior of the plaque, which enhances the effectiveness of such agents. The movement of the bristles creates an alternating pressure field about the teeth while maintaining a bolus of fluid near the bristle tips. When the moving bristles are positioned over the interdental regions, the pressure field created in the fluid by the action of the bristles extends into those regions which are not reached by the bristles themselves.

The pressure on the fluid, which is forced to flow at the bristle tip velocity, is approximately 9 kPa. The pressure falls off with the cosine of the angle of the direction of bristle movement. The pressure will be focused in line with the bristles, primarily toward the periodontal regions and the interdental gap. The best results are achieved when the brush is positioned such that the bristles sweep into and over the gumline, forcing the fluid to move back and forth over that region ahead of the tips of the bristles. The pressure created by the alternating action of the bristles in the fluid is also transmitted through the tissue area, which is typically 0.5–2.0 mm thick. The pressure field thus actually reaches and disrupts the bacteria within the periodontal pocket to a substantial (up to 50%) extent. The actual pressure produced by the oscillating (reciprocating) bristles can be approximated by the well-known formula for pressure produced by an oscillating sphere.

Figure 6:
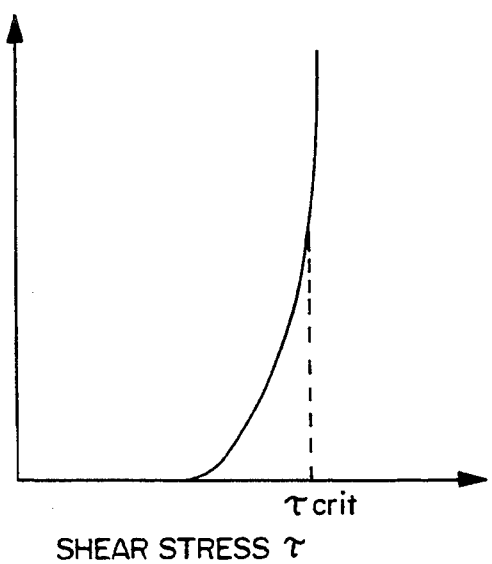
FIG. 6 is a diagram showing the relationship of shear stress on bacteria present on teeth and the rate of dislodgement of the bacteria from the teeth.

A second acoustical effect is the shear stress effect on the bacteria caused by movement of the fluid. Referring to FIG. 5, oral plaque forming bacteria, shown generally at 66, will typically have attachment organelles, referred to as fimbrii or pili, which attach the bacteria to the surface 70 of teeth, as well as to each other. Such bacteria are dislodged from teeth surfaces if the shear stress on the bacteria exceeds a critical value. The critical shear stress for various bacteria will vary according to species. FIG. 6 shows the relationship between shear stress ($\tau$) and the rate of bacterial dislodgement. It has been discovered that when the shear stress exceeds the critical value, a rapid increase in dislodgement occurs. Typical oral bacteria which are attached to dental surfaces have critical shear stresses in the range of 30–300 Pa. The force to produce the required shear stress is provided by the dental fluid flowing back and forth over the tooth. The action of the bristles forces the fluid to flow at a particular velocity (the velocity of the tips of the bristles) across the surface of the teeth, including along the interdental channel between adjacent teeth, where a bolus of fluid is forced to flow.

The initial shear stress is quite high, limited by surface imperfections, e.g. 1000 Pa. Eventually, a boundary layer builds up with a resulting decrease in shear force, with values proportional to bristle tip velocity. Shear stress on the plaque increases significantly when abrasive particles are present in the dental fluid near the surface of the teeth. As an example, a particle in the dental fluid which is moving at 2 m/s at a distance of 10 micrometers from the plaque will result in a shear stress of approximately 10,000 Pa on the plaque, even though the particle itself does not actually contact the plaque. Typically, critical levels of shear stress can be produced on the plaque at distances 2–3 mm from the tips of the bristles with the present invention.

The oscillatory nature of the shear force produced by the vibrating bristles provides added effects in the dislodging or dispersing of attached bacteria. Because the fluid velocity alternates in direction, fatigue is produced in the bacterial attachments. Fatigue fracture of a bacterial bond occurs in proportion to both the level of applied shear force and the number of times the direction of the shear force reverses. Since teeth are brushed only for a relatively short time (the maximum for the entire mouth area is probably about 3 minutes), the higher the frequency of oscillation, the greater the number of times the bacteria will be subjected to the reversing of the direction of the shear force. Accordingly, if the shear force remains the same, a higher frequency will produce fatigue fracture more quickly.

Figure 7:
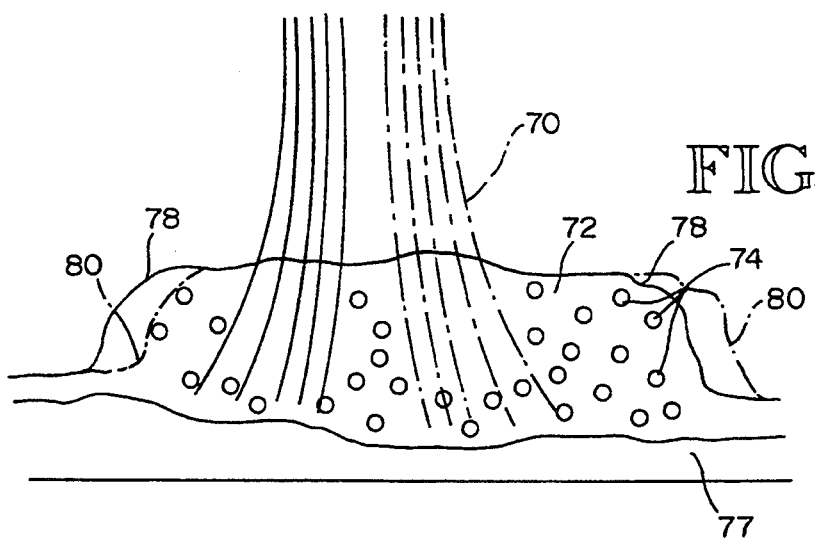
FIG. 7 is a top plan view showing the effect of bristle action of the toothbrush device of the present invention using a dental fluid.

A third acoustical effect of the present invention occurring beyond the tips of the bristles is the abrasive erosion (FIG. 7) created by movement of the bristles 70 in a dental fluid 72 which also contains abrasive particles 74. The fluid 72 flows back and forth by virtue of the action of the bristle tips, which are typically in relatively light actual contact with plaque layer 77. The fluid moves back and forth with the bristles, as indicated by the solid lines 78 and dotted lines 80. The damage which is caused to plaque 77 increases rapidly with the tip velocity of the bristles, since the rate of impact as well as the momentum of the particles in the dental fluid increases with velocity. It has been discovered that below a particular threshold value of bristle velocity, the impact of the particles results in only an elastic stress on the plaque formation, as opposed to actual damage. Thus, significant erosion, like the other acoustic effects, is dependent upon critical velocity levels.

In addition, the bristle movement in a fluid with abrasive particles produces a turbulence in the direction of the flow of the fluid. This turbulent flow is characterized by velocity components in all directions within the fluid, such that the plaque layer is hit by abrasive particles from a variety of angles, rather than strictly along the dental surface as would be the case with laminar flow only.

A fourth significant acoustic effect is produced by the present invention when the bristles rapidly move back and forth, resulting in quantities of air being pulled into the fluid, in a supersaturation effect. This supersaturation effect results in oxygen being present in the fluid around the tips of the bristles significantly above the normal oxygen tension level. This supersaturated fluid then moves into the subgingival regions, for instance, replacing fluid there which may contain very little oxygen. Anaerobic bacteria thrive in those areas, such as the periodontal regions, where there is little or no oxygen present. Significant damage is done to all classes of anaerobic bacteria by the movement of oxygen-containing fluid into those regions. The supersaturation of dental fluid in effect provides a reservoir of oxygen for the periodontal tissues above the normal oxygen tension level, resulting in a longer-term effect on the anaerobic bacteria.

Typically, the more rapidly the bristles vibrate and the greater the amplitude of vibration, the more significant is the capturing of oxygen within the fluid and the greater the effect on the anaerobic bacteria. When the brush moves transversely to the fluid surface, a vertex action results which pulls air into the fluid, and when the bristles reverse direction, the air is entrained in the fluid. The more rapid the movement, the greater the vortex action. Bubbles of oxygen typically are propelled into crevices and pockets of the teeth, as well as the gingival areas. The oxygen bubbles are propelled with such initial velocity that they propagate 2–3 cm outwardly from the tips of the bristles if unimpeded, so they easily reach periodontal pockets remote from the bristle tips. The higher the bristle velocity, the greater the propulsion effect. While the exposure time necessary for effective action will vary depending upon the amplitude of the bristle action, operating within the ranges discussed below will produce significant results.

It should be also understood that the dentifrice itself may contain small bubbles of oxygen and/or oxygen-containing agents such as hydrogen peroxide, which results in an increased effect compared to air as the oxygen source by raising the oxygen tension level above that of atmospheric. In addition, certain active ingredients such as sanguarine, alcohol, various fluorides and chlorhexidine can be used in the dentifrice, and are diffused and/or driven into the crevices of the teeth and the periodontal gingival regions. This can aid in preventing tooth decay. Further, the acoustic effects normally produced by the toothbrush of the present invention as described above will disrupt the plaque matrix, allowing effective penetration of the oxygen and/or the dentifrice agent into the bacterial structure. Also, there may well be a synergistic effect on the anti-bacterial agents when they are used in the pressure field created by the toothbrush of the resent invention.

All of the above-described acoustic effects relative to disruption of plaque occur at pressures less than 10% than that required for vaporous (true) cavitation, which means that the present invention is practical and safe to implement and use at home.

While the scrubbing effect produced by direct contact between the bristles and the plaque is directly dependent on the velocity of the tips of the bristles, the above-described fluid-coupled effects, specifically acoustical pressure, shear stress, abrasive erosion, and oxygen saturation, increase exponentially with the velocity of the bristles, typically between a power of 1.5 and 2.5, depending on the particular effect. The applicants have further discovered that there is a threshold velocity at which point significant acoustic effects begin to occur. In particular, significant cleansing effects occur beyond the bristle tips when the toothbrush is operating within particular critical parameter boundaries.

Figure 8:
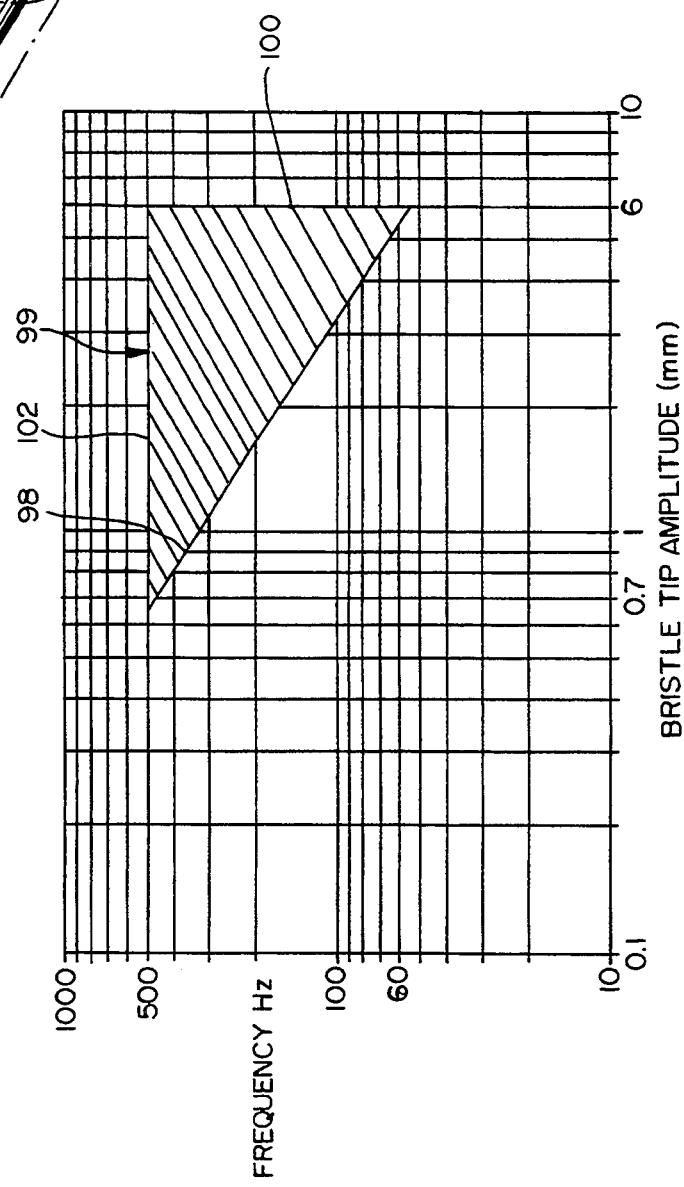
FIG. 8 is a diagram showing critical parameters of frequency and amplitude for the toothbrush of the present invention.

FIG. 8 shows the critical operating regions. One axis shows the amplitude of movement of the bristles, while the other axis shows the frequency of the movement of the tips of the bristles. The velocity of the bristles must be greater than a critical threshold value "$U_{crit}$" in meters/second, in the range of 1.5–2.0 meters/second, for the fluid coupled therapeutic effect to be significant. $U_{crit}$ in turn is determined by frequency and amplitude. The diagonal line 98 in FIG. 8 corresponds to a $U_{crit}$ of 2.0 m/s (although as indicated above, the actual range for U crit is 1.5 m/s to 2.0 m/s). A frequency of 250 Hz and an amplitude of 2.5 mm, which are typical operting parameters, will be within the triangular region 99, which is the critical operating region in FIG. 8. The vertical edge 100 of triangular region 99 corresponds to amplitudes of ±6 mm, beyond which increases in amplitude becomes impractical, because of limited room in the oral cavity. The horizontal edge 102 of region 99 corresponds to frequencies of 500 Hz, above which increases in frequency are irritating to human hearing and are above the resonant frequency of the bristles. An appropriate frequency range is 40 Hz–500 Hz and an appropriate amplitude range is 0.5 mm–6 mm.

The critical region 99 is remote from the operating characteristics of other known power toothbrushes and when the toothbrush of the present invention is operated within this region, significant cleansing effects are achieved beyond the bristle tips. The present invention also produces acoustic pressure levels far above other commercial power toothbrushes. Typically, a threshold acoustic pressure level is 1.5 kPa.

In addition to the above, the tooth brush will be constructed so that the operating frequency of the bristles is below their resonant frequency, but close enough thereto to permit a bristle amplitude greater than the amplitude of the plate on which the bristles are mounted. Bristle movement is also typically 2-3 times that of the resonance arm. This facilitates driving the bristle tips to the desired velocity without having to drive the coupling elements, such as the resonance arm, the full amplitude of the bristle tips.

In summary, a range of bristle tip velocities has been discovered, for a power toothbrush, including specific ranges of tip frequency and amplitude, which results in significant therapeutic effects beyond the physical reach of the tips of the bristles, by virtue of the action of the bristles in a surrounding dentifrice fluid.

Although a preferred embodiment of the invention has been disclosed herein for illustration, it should be understood that various changes, modifications and substitutions may be incorporated in such embodiment without departing from the spirit of the invention which is defined by the claims which follow:

What is claimed is:

1. A dental hygiene device for cleaning teeth and interdental and gingival areas, comprising:

a body member which includes an arm mounted for movement;

a set of bristles having free end tips, the set of bristles being located in the vicinity of one end of the arm; and means in the body member for moving the arm and hence the set of bristles such that the tips of the bristles move at a velocity greater than approximately 1.5 meters per second, which is sufficient to produce a cleansing action with a dentifrice fluid beyond the tips of the bristles.

2. An apparatus of claim 1, wherein the velocity of the bristle tips is at least 2.0 meters per second.

3. An apparatus of claim 1, wherein the cleansing action reaches the interdental and gingival areas without the tips of the bristles being in the immediate vicinity thereof.

4. An apparatus of claim 1, wherein the frequency of movement of the tips of the bristles is between 40 Hz and 500 Hz, and wherein the amplitude of movement of the bristles is within the range of 0.5 mm to 6 mm.

5. An apparatus of claim 4, wherein the frequency is less than the resonant frequency of the bristles.

6. An apparatus of claim 1, wherein shear stress on dental plaque created by action of the apparatus is greater than 50 Pa at a distance of 2 mm from the tips of the bristles.

7. An apparatus of claim 1, wherein the movement of the bristles produces an acoustic pressure of at least 1.5 kPa.

8. An apparatus of claim 1, wherein the bristles extend substantially perpendicularly relative to the arm and wherein the tips of the bristles move in a single plane.

9. An apparatus of claim 1, wherein the set of bristles rotate through a preselected arc.

10. An apparatus of claim 1, wherein the tips of the bristles re scalloped with each scalloped portion being in the range of 5–8 mm long, with a depth of 1.5–3 mm.

11. A method for cleaning teeth and interdental and gingival areas, using a toothbrush apparatus having a moving arm with a set of bristles at one end thereof, comprising the steps of:

providing dental fluid in the vicinity of the teeth and interdental and gingival areas to be cleaned; and moving the arm and hence the bristles such that the tips of the bristles move through the dental fluid at a velocity greater than approximately 1.5 meters per second, thereby producing a cleansing effect, through corresponding movement of the dental fluid, beyond the tips of the bristles.

12. A method of claim 11, wherein the velocity of the bristle tips is greater than 2.0 meters per second.

13. A method of claim 11, wherein the cleansing effect reaches the interdental and gingival areas without the tips of the bristles being in the immediate vicinity thereof.

14. A method of claim 11, wherein the frequency of movement of the tips of the bristles is between 40 Hz and 500 Hz and wherein the amplitude of movement is within the range of 0.5 mm to 6 mm.

15. A method of claim 14, wherein the frequency is less than the resonant frequency of the bristles.

16. A method of claim 11, wherein movement of the bristles produces an acoustic pressure of at least 1.5 kPa.

17. A method of claim 11, whereon the motion of said bristles is in a single plane, such that when the bristles are positioned horizontally against the tooth, the tips of the bristles move vertically toward and away from the gum line.

18. A method of claim 11, wherein the set of bristles rotates through a preselected arc.

19. A method of claim 11, wherein the dental fluid contains abrasive particles.

20. A method of claim 11, wherein the dental fluid contains oxygen-releasing agents.

21. A method of claim 11, wherein the dental fluid contains an anti-bacterial agent.

22. A dental hygiene device for cleaning teeth and interdental and gingival areas, comprising:

a body member which includes an arm mounted for movement;

a set of bristles having free end tips, the set of bristles being located in the vicinity of one end of the arm; and means in the body member for moving the arm and hence the set of bristles such that the tips of the bristles move at a sufficient velocity to create an alternating pressure field in a dental fluid sufficient that the dental fluid flows in alternate opposing directions at approximately the speed of the bristles, wherein the frequency of movement of the tips of the bristles is between 40 Hz and 500 Hz, wherein the amplitude of movement of the bristles is within the range of 0.5 mm to 6 mm, and wherein the movement of the bristles produces an acoustic pressure of at least 1.5 kPa the dental fluid being in contact with the teeth and the interdental and gingival areas, the alternating pressure field being sufficient to significantly damage dental plaque in the interdental and gingival areas without physical contact between the bristles and the plaque.

23. An apparatus of claim 22, wherein the velocity of the bristles is approximately at least 1.5 meters per second.

24. A method for cleaning teeth and interdental and gingival areas, using a toothbrush apparatus having a moving arm with a set of bristles at one end thereof, comprising the steps of:

providing dental fluid in the vicinity of the teeth and interdental and gingival areas to be cleaned; and moving the arm and hence the bristles such that the tips of the bristles move at a sufficient velocity to create an alternating pressure field in the dental fluid sufficient that the dental fluid flows in alternate opposing directions at approximately the speed of the bristles, wherein the frequency of movement of the tips of the bristles is between 40 Hz and 500 Hz, wherein the amplitude of movement of the bristles is within the range of 0.5 mm to 6 mm, and wherein the movement of the bristles produces an acoustic pressure of at least 1.5 kPa, the alternating pressure field being sufficient to significantly damage dental plaque without physical contact between the bristles and the plaque.

25. A method of claim 24, wherein the dental fluid contains abrasive particles, which increases the damage to the dental plaque.

26. A method of claim 24, wherein the dental fluid contains oxygen-releasing agents.

27. A method of claim 24, wherein the dental fluid contains an anti-bacterial agent.

28. A dental hygiene device for cleaning teeth and interdental and gingival areas, comprising:

a body member which includes an arm mounted for movement;

a set of bristles having free end tips, the set of bristles being located in the vicinity of one end of the arm; and means in the body member for moving the arm and hence the set of bristles such that the tips of the bristles move at a frequency between 40 Hz and 500 Hz, and wherein the amplitude of movement of the bristles is within a range of 0.5 mm to 6 mm, wherein the velocity of the tips of the bristles is sufficient to produce a shear stress, approximately at least 50 Pa, on bacteria on the teeth in the interdental and gingival areas sufficient to dislodge said bacteria without physical contact between the bristles and the bacteria.

29. An apparatus of claim 28, wherein the velocity of the bristles is approximately at least 1.5 meters per second.

30. A method for cleaning teeth and interdental and gingival areas, using a toothbrush apparatus having a moving arm with a set of bristles at one end thereof, comprising the steps of:

providing dental fluid in the vicinity of the teeth and interdental and gingival areas to be cleaned; and moving the arm and hence the bristles such that the tips of the bristles move at a frequency between 40 Hz and 500 Hz, and wherein the amplitude of movement of the bristles is within the range of 0.5 mm to 6 mm, wherein the velocity of the tips of the bristles is sufficient to produce shear stress, approximately at least 50 Pa, on bacteria on the teeth in the interdental and gingival areas sufficient to dislodge said bacteria without physical contact between the bristles and the bacteria.

31. A method of claim 30, wherein the dental fluid contains abrasive particles, which increases the dislodgement of the bacteria.

32. A method of claim 30, wherein the dental fluid contains oxygen-releasing agents.

33. A method of claim 30, wherein the dental fluid contains an anti-bacterial agent.

34. A dental hygiene device for cleaning teeth and interdental and gingival areas, comprising:
- a body member which includes an arm mounted for movement;
- a set of bristles having free end tips, the set of bristles being located in the vicinity of one end of the arm; and
- means in the body member for moving the arm and hence the set of bristles such that the tips of the bristles move at a frequency between 40 Hz and 500 Hz, and wherein the amplitude of movement of the bristles is within the range of 0.5 mm to 6 mm, wherein the velocity of the tips of the bristles is greater than approximately 1.5 meters per second, such that dental fluid which is in contact with the teeth becomes supersaturated with oxygen, wherein the oxygen present in the dental fluid around the tips of the bristles is significantly above the normal oxygen tension level, resulting in a substantial reduction in the level of anaerobic bacteria in the gingival regions as the supersaturated dental fluid moves into those regions.

35. A method for cleaning teeth and interdental and gingival areas, using a toothbrush apparatus having a moving arm with a set of bristles at one end thereof, comprising the steps of:
- providing dental fluid in the vicinity of the teeth and interdental and gingival areas to be cleaned; and
- moving the arm and hence the bristles such that the tips of the bristles move at a frequency between 40 Hz and 500 Hz, and wherein the amplitude of movement of the bristles is within the range of 0.5 mm to 6 mm, wherein the velocity of the tips of the bristles is greater than approximately 1.5 meters per second, such that the dental fluid becomes supersaturated with oxygen, wherein the oxygen present in the dental fluid around the tips of the bristles is significantly above the normal oxygen tension level, resulting in a substantial reduction in the level of anaerobic bacteria in the gingival regions as the supersaturated dental fluid moves into those regions.

* * * * *